United States Patent [19]

O'Reilly et al.

[11] Patent Number: 5,233,085
[45] Date of Patent: Aug. 3, 1993

[54] PREPARATION OF 2,4,5-TRIFLUOROBENZOIC ACID BY DECARBOXYLATION OF 3,4,6-TRIFLUOROPHTHALIC ACID

[75] Inventors: Neil J. O'Reilly, Grand Island; William S. Derwin, Buffalo; Henry C. Lin, Grand Island, all of N.Y.

[73] Assignee: Occidental Chemical Corporation, Niagara Falls, N.Y.

[21] Appl. No.: 896,869

[22] Filed: Jun. 12, 1992

Related U.S. Application Data

[63] Continuation-in-part of Ser. No. 439,229, Nov. 20, 1989, abandoned.

[51] Int. Cl.$^5$ ............................ C07C 51/377; C07C 63/10
[52] U.S. Cl. .................................. 562/479; 562/494
[58] Field of Search ............................ 562/479

[56] References Cited

U.S. PATENT DOCUMENTS 4,782,180  11/1988  Wemple et al. .................... 562/479

OTHER PUBLICATIONS

Yakobson et al., "Zh. Obsch. Khim 36" (1966) pp. 139–142 (in J. Gen. Chem. USSR, translated from Russian, 36 (1966) pp. 144–146.

Primary Examiner—Joseph E. Evans
Attorney, Agent, or Firm—Wayne A. Jones; Arthur S. Cookfair; Richard D. Fuerle

[57] ABSTRACT 3,4,6-Trifluorophthalic acid may be decarboxylated in a controlled manner to form 2,4,5-trifluorobenzoic acid by heating the phthalic acid in a dipolar aprotic solvent in the absence of any catalyst.

4 Claims, No Drawings

PREPARATION OF 2,4,5-TRIFLUOROBENZOIC ACID BY DECARBOXYLATION OF 3,4,6-TRIFLUOROPHTHALIC ACID

This invention is a continuation-in-part of U.S. application Ser. No. 07/439,229, filed Nov. 20, 1989 now abandoned.

BACKGROUND OF THE INVENTION

This invention relates to a method for the preparation of 2,4,5-trifluorobenzoic acid by the decarboxylation of 3,4,6-trifluorophthalic acid. 2,4,5-trifluorobenzoic acid is a useful intermediate in the manufacture of quinolone antibacterial drugs.

Heretofore, 2,4,5-trifluorobenzoic acid has been difficult to synthesize. One known method of synthesis involves the cyanation of 2,4,5-trifluorobromobenzene using copper cyanide in dimethyl formamide, followed by hydrolysis of the product nitrile with sulfuric acid [Sanchez, J. P. et al *J. Med. Chem.* (1988), 31, 983]. This synthetic method is difficult to use, and expensive.

We have now discovered that 2,4,5-trifluorobenzoic acid may be prepared by the decarboxylation of 3,4,6-trifluorophthalic acid. The reaction may be conducted in dipolar aprotic solvents, without the use of a catalyst. Surprisingly, only one of the two carboxyl groups is removed, and 2,4,5-trifluorobenzoic acid is produced in good yield. 3,4,6-Trifluorophthalic acid may be conveniently prepared from 3,4,6-trichlorophthalic acid. The acid is reacted with aniline to form 3,4,6-N-phenylphthalimide. The phthalimide is then treated with potassium fluoride in sulfolane using tributylhexadecylphosphonium bromide as a phase transfer catalyst. The method is disclosed in copending patent application Ser. No. 07/315,746, which is hereby specifically incorporated by reference.

Many examples of decarboxylation reactions have been reported. Basic substances have been used to catalyze such reactions. For example, it is disclosed in D. S. Tarbell, et al Org. Syn., III coll. vol. (1955) 267, that 3,5-dichloro-4-hydroxybenzoic acid may be decarboxylated by vigorous heating in N,N-dimethylaniline. It is disclosed in A. Singer and S. M. McElvane, Org. Syn., coll. vol. II (1943) 214, that 3,5-dicarboxy-2,6-dimethylpyridine di-potassium salt may be completely decarboxylated by heating the salt in the presence of calcium hydroxide. Copper and copper salts have been used to catalyze decarboxylation reactions. For example, H. R. Snyder et al, Org. Syn., coll. vol. III (1955) 471 disclose the use of copper oxide catalyst for the decarboxylation of imidazole-4,5-dicarboxylic acid.

Some compounds may be decarboxylated without catalysts. For example, C. Wang, Bul. Inst. Kim. Acad. Sinica, no. 2156 (1972), as abstracted in CA79 (15):91729, discloses that tetrachloro or tetrabromophthalic acids, or their anhydrides, may be decarboxylated to the corresponding benzoic acids when refluxed in dimethyl formamide. 3-nitrophthalic acid underwent a similar reaction. Under similar conditions 1,8-naphthalene dicarboxylic acid, and its 3-nitro derivative merely formed the corresponding anhydride.

Decarboxylation is not always a predictable reaction. For example, A. S. Sultanov, J. Gen. Chem. (USSR) 16 1835 (1946) as abstracted in CA 41:6223(e) discloses that salicylic acid may be decarboxylated by autoclaving the acid in the presence of copper bronze and benzene at 170° C. The acid alone decarboxylates at 205° C., while in the presence of aniline decarboxylation begins at 170° C. In the case of salicylic acid, aniline and copper bronze seem to be equal in catalytic ability. On the other hand, when phthalic acid is heated in aniline at 180° C., decarboxylation does not occur and instead phthalic anhydride is produced. Heating phthalic anhydride with copper bronze in chloroform at 180° C. gave a 22% yield of benzoic acid. Phthalic acid was found to decarboxylate to yield benzoic acid merely by heating in water at 235° C.

Decarboxylations of certain fluorophthalic acids have been reported. 3,4,5,6-tetrafluorophthalic acid decarboxylates under certain conditions to yield 2,3,4,5-tetrafluorobenzoic acid. For example, Japanese Patent JP 61/85349 A2[86/85349] as abstracted in CA105:152719r discloses that the reaction may be conducted in an aqueous medium at 150° to 230° C. The reaction may be carried out at lower temperature (100° to 250° C.) in the presence of copper, zinc, cadmium, iron, cobalt, nickel, other oxides, hydroxides and/or carbonates. Japanese Patent Application 86/103,317 as abstracted in CA105 (22):193368u discloses that the above reaction may be conducted in an aqueous medium at a pH of 0.7-2.2 at a temperature of 100°-200° C. The pH of the medium is adjusted by acidifying with sulfuric acid and partial neutralization with calcium hydroxide. Japanese Patent 63/295529m A2[88/295529] (as abstracted in Chem. Abstracts CA 111 (3): 23221X) discloses that the reaction may be conducted at 130° in tri-butylamine.

Small changes in structure of molecule, or conditions can result in major changes in the product produced when fluorinated phthalic acids are decarboxylated. For example, Yacobsen, O. J. discloses in Zh. Obsch. Khim. 36 (1966) page 139 (as appearing in Journal of General Chemistry of the U.S.S.R., translated from Russian, 36 (1966) page 144), that 3,4,5,6-tetrafluorophthalic acid may be decarboxylated to yield 44% 2,3,4,5-tetrafluorobenzoic acid by heating for one hour at 145° C. in dimethyl formamide. An unspecified amount of tetrafluorobenzene was found but it was not clear whether or not the amount of tetrafluorobenzene found accounts for the remainder of the starting material.

Under slightly more vigorous conditions, Japanese Patent Application 61/43130 A2[86/43130]as abstracted in CA106 (1):4629S and Derwent, accession number 86-097893/15, discloses that 3,4,5,6-tetrafluorophthalic acid may be completely decarboxylated to 1,2,3,4-tetrafluorobenzene in an aqueous medium from 210° to 300° C. In the presence of a catalyst, such as powdered metallic copper, zinc, cadmium, iron, cobalt or nickel or acids, hydroxides or carbonates of those metals the complete decarboxylation proceeds at temperatures as low as 100° C. and preferably from 160°-240° C.

U.S. Pat. No. 4,782,180 discloses that 3,4,5,6-tetrafluoropthalic acid may be decarboxylated to form tetrafluorobenzoic acid. The reaction may be carried out in polar aprotic solvents and requires the presence of a base catalyst. Although organic amines are preferred, inorganic bases such as sodium bicarbonate, potassium carbonate, and sodium hydroxide may also be used. Potassium carbonate as a catalyst apparently leads to monodecarboxylation, whereas the carbonate of copper, zinc, cadmium, iron, cobalt, or nickel would lead to total decarboxylation, as reported in Japanese Patent application 61/43130 A2 (86/43130).

U.K. Patent 2,122,190 discloses that tetrafluoroterphthalic acid, in which the carboxyl groups are para to one another, readily decarboxylates in polar aprotic solvents to form 1,2,4,5-tetrafluorobenzene. The process may be conducted at temperatures as low as 100° C. No catalyst is required, although a copper oxide catalyst may be used if desired.

Japanese Patent Application 86/290399 as abstracted in CA109 (19) 170038e discloses that 3,5,6-trifluoro-4-hydroxyphthalic acid may be decarboxylated by heating the compound for three hours, in water, under nitrogen atmosphere, at 140° C. (in a sealed tube) to yield 2,4,5-trifluoro-3-hydroxybenzoic acid.

Aroskar et al (J. Chem. Soc. (1964) 2975) discloses a method for preparing 3,4,6-trifluorophthalic acid. They found that upon slowly heating a mixture of the acid and soda lime to 300° C., they obtained a low yield of the fully decarboxylated 1,2,4-trifluorobenzene.

Japanese Patent JP 01/52737 discloses the preparation of 2,4,5-trifluorobenzoic acid by the decarboxylation of 3,4,6-trifluorophthalic acid in a liquid medium at a temperature of 80°-250° C. The liquid media disclosed include water, DMSO, tetramethyl sulfone, DMF, dimethylacetamide, N-methylpyrrolidone, acetonitrile, nitrobenzene, diethylene glycol, dimethyl ether, tetraethylene glycol, dimethyl ether, and tertiary amines such as tributyl amine, and dimethyl aniline. The patent further discloses that a catalyst such as the ammonium or alkaline earth metal salts of hydroxide, carbonate, bicarbonate, sulfate or fluoride may be used.

In U.S. Pat. No. 4,935,541, the present inventors have disclosed a process for the preparation of 2,4,5-trifluorobenzoic acid by decarboxylation of 3,4,6-trifluorophthalic anhydride at elevated temperatures in apolar, aprotic solvent, preferably in the presence of a copper catalyst.

SUMMARY OF THE INVENTION

Surprisingly, we have now found that 3,4,6-trifluorophthalic acid may be decarboxylated in a controlled manner to form 2,4,5-trifluorobenzoic acid by heating the phthalic acid in a dipolar aprotic solvent in the absence of any catalyst.

DETAILED DESCRIPTION OF THE INVENTION

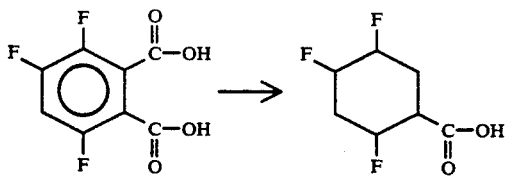

According to the present invention, 2,4,5-trifluorobenzoic acid may be prepared in good yield by the decarboxylation of 3,4,6-trifluorophthalic acid. The decarboxylation process is not complex. The acid is dissolved in the appropriate solvent and the mixture is heated along with stirring, until the desired percentage of starting material has been converted to products. At any point in the reaction, the degree of conversion of starting materials to products can readily be judged by gas chromatographic analysis. However, the reaction is reproducible and once convenient conditions within the scope of this invention have been established for conducting the reaction, the gas chromatographic analysis need not be conducted routinely.

The desired product of this reaction is 2,4,5-trifluorobenzoic acid. However, it can readily be seen that the two carboxyl groups in the 3,4,6-trifluorophthalic acid molecule are not equivalent to each other. The removal of the carboxyl at position 2 leads to the desired product, while the removal of the carboxyl at position one leads to 2,3,5-trifluorobenzoic acid. The 2,3,5-product is not desired and the methods of this invention minimize its formation.

In the present process it has been found that a dipolar aprotic solvent such as dimethyl formamide, dimethyl acetamide, dimethyl sulfoxide, and N-methylpyrrolidone is appropriate. The foregoing list of dipolar aprotic solvents is not exclusive and other such solvents may be used in practicing this invention. The preferred solvents are dimethyl sulfoxide, dimethyl acetamide and N-methylpyrrolidone, the most preferred solvent is N-methylpyrrolidone. It has been found that the reaction may be conducted in a temperature range from about 125°-190° C. The preferred temperature is approximately 150° C.

Surprisingly, copper catalysts, which are well known for use in decarboxylation reactions, are not useful for the preparation of 2,4,5-trifluorobenzoic acid (2,4,5-TiFBA) from 3,4,6-trifluorophthalic acid. reaction. As can be seen from the table below, the copper catalysts increase the rate of the reaction, but produce high percentage of the undesired 2,3,5-trifluorobenzoic acid (2,3,5-TiFBA).

| 3,4,6-trifluorophthalic Acid Decarboxylation Catalyst Study 150° C. in Dimethyl Acetamide | | | | |
|---|---|---|---|---|
| | | Gas Chromatography Area % | | |
| Catalyst | Period | 2,4,5-TiFBA | 2,3,5-TiFBA | Ratio |
| none | 4 hr. | 81% | 5% | 16.2 |
| Cu | 0.5 hr. | 65% | 27% | 2.4 |
| Cu$_2$O | 0.5 hr. | 62% | 31% | 2.0 |
| CuO | 1.5 hr. | 77% | 18% | 4.3 |
| CuI | 1.5 hr. | 59% | 21% | 2.8 |

Similarly, the use of basic catalysts such as organic amines or inorganic bases is not necessary. Furthermore, the presence of a catalyst introduces an unnecessary and undesirable impurity to be removed form the final product. Accordingly, the process is conducted in the absence of any catalyst.

The 2,4,5-trifluorobenzoic acid produced by this process contains some impurities of 2,3,5-trifluorobenzoic acid as well as other minor impurities. If a higher purity product is desired, the reaction product may be readily purified by known methods such as chromatography on silica gel and recrystallization.

The following specific examples are provided to further illustrate this invention and the manner in which it may be carried out. It will be understood, however, that the specific details given in the examples have been chosen for purposes of illustration and are not to be construed as a limitation on the invention. In the examples, unless otherwise indicated, all parts and percentages are by weight and al temperatures are in degrees Celsius.

EXAMPLE 1 Perforation of 2,4,5-Trifluorobenzoic Acid by the Decarboxylation of 3,4,6-Trifluorophthalic Acid in N-Methylpyrrolidone (NMP)

A 250 mL single-neck flask equipped with a condenser and a magnetic stirrer was charged with 30.00 g of 3,4,6-trifluorophthalic acid, and 200 mL of NMP. The reaction mixture was then heated with stirring for 18 hr. at a bath temperature of 140° C., followed by 55 hr. at a bath temperature of 150° C. The flask was then allowed to cool to room temperature and the contents were poured into 500 mL of water, and extracted with 4×200 mL of ethyl acetate. The combined organic extracts were washed with water (2×200 mL), dried over magnesium sulfate, filtered, and the solvent removed on a rotary evaporator followed by drying at the pump overnight. The crude product (24.25 g) was then dissolved in 25 mL of ethyl acetate and introduced at the top of a silica column (4.5 cm ID×56 cm, flushed with hexane). The product was then eluted with 90:10 hexane:ethyl acetate under a slight nitrogen pressure, and the fractions (500 mL each) were monitored by gas chromatography. The fractions containing the product were combined, the solvent removed on a rotary evaporator, and then dried at the pump overnight to give 2,4,5-trifluorobenzoic acid as a light yellow solid (21.06 g, 98.97% pure, 87.8% yield). Recrystallization of the product from toluene (50 mL, ca. 60° C.) gave a white product (71.1% overall yield) mp 101°–102° C.

EXAMPLE 2 Preparation of 2,4,5-Trifluorobenzoic Acid by the Decarboxylation of 3,4,6-Trifluorophthalic Acid in Dimethyl sulfoxide(DMSO)

A 250 mL single-neck flask equipped with a condenser and a magnetic stirrer was charged with 30.00 g of 3,4,6-trifluorophthalic acid, and 200 mL of dimethyl sulfoxide. The reaction mixture was then heated with stirring for 27.5 hr. at a bath temperature of 149° C. The flask was then allowed to cool to room temperature and the contents were poured into 500 mL of water, and extracted with 4×200 mL of ethyl acetate. The combined organic extracts were washed with water (2×200 mL), dried over magnesium sulfate, filtered, and the solvent removed on a rotary evaporator followed by drying at the pump overnight. The crude product was then dissolved in 25 mL of ethyl acetate and introduced at the top of a silica column (4.5 cm ID×56 cm, flushed with hexane). The product was then eluted with 90:10 hexane:ethyl acetate under a slight nitrogen pressure, and the fractions (500 mL each) were monitored by gas chromatography. The fractions containing the product were combined, the solvent removed on a rotary evaporator, and then dried at the pump overnight to give 2,4,5-trifluorobenzoic acid as a light yellow solid. Recrystallization of the product from toluene (50 mL, ca. 60° C.) gave a white product (66.9% overall yield).

EXAMPLE 3 Preparation of 2,4,5-Trifluorobenzoic Acid by the Decarboxylation of 3,4,6-Trifluorophthalic Acid in Dimethyl Acetamide (DMAc)

A 250 mL single-neck flask equipped with a condenser and a magnetic stirrer was charged with 30.00 g of 3,4,6-trifluorophthalic acid, and 200 mL of dimethyl acetamide. The reaction mixture was then heated with stirring for 29.2 hr. at a bath temperature of 127° C. The flask was then allowed to cool to room temperature and the contents were poured into 500 mL of water, and extracted with 4×200 mL of ethyl acetate. The combined organic extracts were washed with water (2×200 mL), dried over magnesium sulfate, filtered, and the solvent removed on a rotary evaporator followed by drying at the pump overnight. The crude product was then dissolved in 25 mL of ethyl acetate and introduced at the top of a silica column (4.5 cm ID×56 cm, flushed with hexane). The product was then eluted with 90:10 hexane:ethyl acetate under a slight nitrogen pressure, and the fractions (500 mL each) were monitored by gas chromatography. The fractions containing the product were combined, the solvent removed on a rotary evaporator, and then dried at the pump overnight to give 2,4,5-trifluorobenzoic acid as a light yellow solid. Recrystallization of the product from toluene (50 mL, ca. 60° C.) gave a white product (65.0% overall yield).

EXAMPLE 4 Preparation of 2,4,5-Trifluorobenzoic Acid by the Decarboxylation of 3,4,6-Trifluorophthalic Acid in Dimethyl Acetamide(DMAc)

A 10 mL single-neck flask equipped with a condenser and a magnetic stirrer was charged with 0.2 g of 3,4,6-trifluorophthalic acid, and 200 mL of dimethyl acetamide. The reaction mixture was then heated with stirring for 22 hr. at a bath temperature of 125° C. followed by 2 hr. at a bath temperature of 150° C. The flask was then allowed to cool to room temperature and the contents were analyzed by gas chromatography. The percentage of the total peak area corresponding to 2,4,5-trifluorobenzoic acid was 86%.

EXAMPLE 5 Preparation of 2,4,5-Trifluorobenzoic Acid by the Decarboxylation of 3,4,6-Trifluorophthalic Acid in Dimethyl Sulfoxide (DMSO)

A 10 mL single-neck flask equipped with a condenser and a magnetic stirrer was charged with 0.2 g of 3,4,6-trifluorophthalic acid, and 200 mL of dimethyl sulfoxide. The reaction mixture was then heated with stirring for 22 hr. at a bath temperature of 125° C. followed by 11 hr. at a bath temperature of 150° C. The flask was then allowed to cool to room temperature and the contents were analyzed by gas chromatography. The percentage of the total peak area corresponding to 2,4,5-trifluorobenzoic acid was 96%.

EXAMPLE 6 Preparation of 2,4,5-Trifluorobenzoic Acid by the Decarboxylation of 3,4,6-Trifluorophthalic Acid in N-Methylpyrrolidone (NMP)

A 10 mL single-neck flask equipped with a condenser and a magnetic stirrer was charged with 0.2 g of 3,4,6-trifluorophthalic acid, and 2 mL of N-methylpyrrolidone. The reaction mixture was then heated with stirring for 4.4 hr. at a bath temperature of 125° C. followed by 4.7 hr. at a bath temperature of 150° C. The flask was then allowed to cool to room temperature and the contents were analyzed by gas chromatography. The percentage of the total peak area corresponding to 2,4,5-trifluorobenzoic acid was 97%.

EXAMPLE 7 Preparation of 2,4,5-Trifluorobenzoic Acid by the Decarboxylation of 3,4,6-Trifluorophthalic Acid in Dimethyl Formamide (DMF)

A 10 mL single-neck flask equipped with a condenser and a magnetic stirrer was charged with 0.2 g of 3,4,6-trifluorophthalic acid, and 2 mL of dimethyl formamide. The reaction mixture was then heated with stirring for 22 hr. at a bath temperature of 125° C. The flask was then allowed to cool to room temperature and the contents were analyzed by gas chromatography. The percentage of the total peak area corresponding to 2,4,5-trifluorobenzoic acid was 63%.

We claim:

1. A process for the production of 2,4,5-trifluorobenzoic acid which comprises dissolving 3,4,6-trifluorophthalic acid in a dipolar aprotic solvent, in the absence of a catalyst, to obtain solution, and heating said solution until the 3,4,6-trifluorophthalic acid has been consumed.

2. A process according to claim 1 wherein the solvent is dimethyl sulfoxide and the reaction is conducted at a temperature between 125° and 190° C.

3. A process according to claim 1 wherein the solvent is dimethyl acetamide and the reaction is conducted at a temperature between 125° and 190° C.

4. A process according to claim 1 wherein the solvent is N-methylpyrrolidone and the reaction is conducted at a temperature between 125° and 190° C.

* * * * *